United States Patent
Coakley et al.

(10) Patent No.: US 6,719,686 B2
(45) Date of Patent: *Apr. 13, 2004

(54) FETAL PROBE HAVING AN OPTICAL IMAGING DEVICE

(75) Inventors: Joe Coakley, Dublin, CA (US); John Walsh, Berkeley, CA (US); Michael E. Fein, deceased, late of Mountain View, CA (US), by Marcia Fein, legal representative; Bryan Weber, Livermore, CA (US)

(73) Assignee: Mallinckrodt, Inc., Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/921,287

(22) Filed: Aug. 1, 2001

(65) Prior Publication Data

US 2002/0068852 A1 Jun. 6, 2002

Related U.S. Application Data

(60) Provisional application No. 60/229,368, filed on Jun. 19, 2001.

(51) Int. Cl.⁷ .............................. A61B 1/00; A61B 5/04
(52) U.S. Cl. ........................ 600/170; 600/103; 600/376
(58) Field of Search .............................. 600/103, 104, 600/115, 116, 170, 118, 167, 182, 388, 376, 511

(56) References Cited

U.S. PATENT DOCUMENTS

| | | | | |
|---|---|---|---|---|
| 3,690,769 A | * | 9/1972 | Mori | 356/41 |
| 4,224,929 A | | 9/1980 | Furihata | |
| 5,323,776 A | * | 6/1994 | Blakeley et al. | 600/324 |
| 5,419,312 A | | 5/1995 | Arenberg et al. | |
| 5,547,455 A | * | 8/1996 | McKenna et al. | 600/113 |
| 5,681,277 A | * | 10/1997 | Edwards et al. | 604/22 |
| 5,916,155 A | | 6/1999 | Levinson et al. | |
| 5,987,351 A | * | 11/1999 | Chance | 600/473 |
| 6,134,460 A | * | 10/2000 | Chance | 600/342 |
| 6,277,066 B1 | | 8/2001 | Irwin | |

* cited by examiner

*Primary Examiner*—John P. Leubecker
(74) *Attorney, Agent, or Firm*—Townsend and Townsend and Crew LLP

(57) ABSTRACT

Systems and methods for providing visual feedback to aid in the proper placement and location of a fetal sensor during a fetal oximetry monitoring procedure. An imaging device, such as an optical fiber can be used to image and illuminate the same or nearby region of tissue which the fetal sensor contacts. The image from the illuminated portion of tissue is transmitted along the optical fiber to an optical viewing device such as a hand-held image viewing instrument, camera, or an image processor/video display.

15 Claims, 3 Drawing Sheets

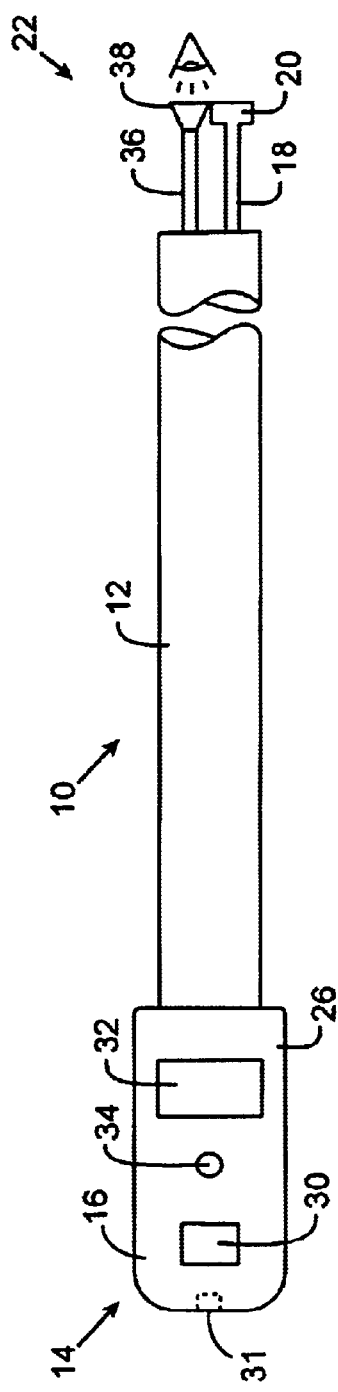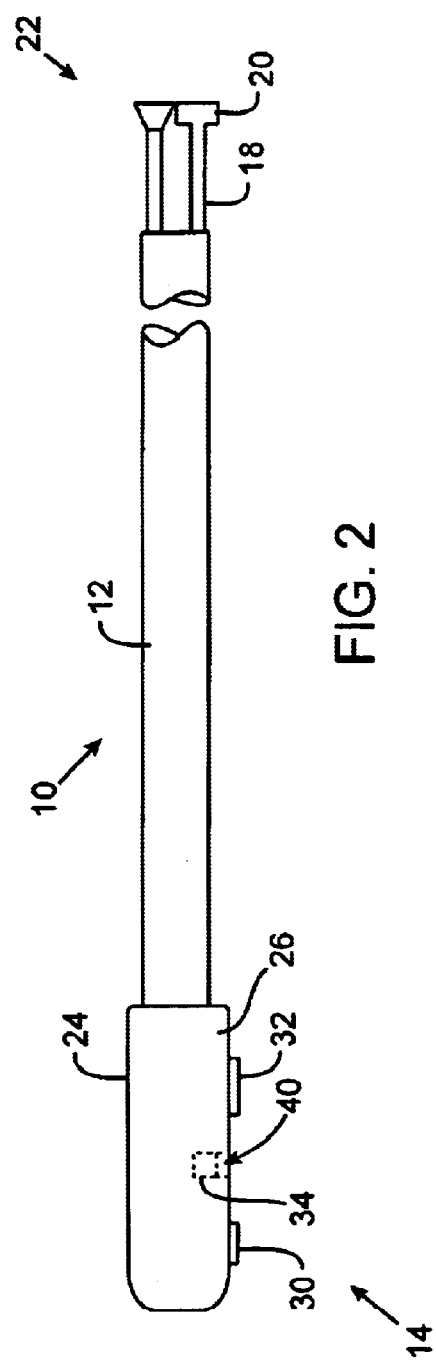

FETAL PROBE HAVING AN OPTICAL IMAGING DEVICE

The present application claims benefit of Provisional Patent Application Ser. No. 60/229,368, filed Jun. 19, 2001, and entitled "A Fetal Probe Having an Optical Imaging Device," and is related to U.S. patent application Ser. No. 09/920,996, filed concurrently herewith, entitled "Balloon Assisted Endoscope For Viewing A Fetus During Delivery." now U.S. Pat. No. 6,659,941, the complete disclosures of which are incorporated herein by reference for all

BACKGROUND OF THE INVENTION

The present invention relates generally to fetal probes for monitoring the condition of a fetus in utero and more specifically to a fetal probe having an optical imaging device.

During in utero labor and delivery of a fetus, fetal probes are used to monitor the health of the fetus. Fetal probes having pulse oximeters are typically used to measure various blood characteristics including arterial blood oxygen saturation and pulse rate. Pulse oximetry sensors pass light through a portion of the fetus' skin and photo-electrically detect pulsatile changes in the absorption of the light by the tissue. The detected light is then used to determine the characteristic of interest.

In order to achieve accurate measurements, the aforementioned sensing devices must maintain contact with the fetus at an appropriate part of the fetus' body. The quality of the optical signal generated by the pulse oximeter sensor depends, in part, on the placement of the sensors on the fetus' body and on the quality of optical coupling between the sensor and the patient. The quality of optical coupling is related to the amount of light emitted by the sensor that actually enters the fetus' tissue and to the portion of the light received by the sensor that actually passes through the fetus' blood-perfused tissue.

Tissue characteristics at the sensor site can affect the quality of the optical coupling between the sensor and the patient. The presence of hair or vernix on the skin will attenuate the light transmitted into the tissue by the sensor. For example, if the sensor is placed on a part of the fetus' scalp the system may not be able to appropriately process the signal. Consequently, it is important that the physician position and orient the fetal probe at a proper place on the fetus.

One method of placing the fetal probe adjacent the fetus is through manual assessment of the womb to determine the orientation of the head of the fetus and depth of the fetus within the womb. Once the physician has determined the position of the fetus, the physician picks a line of entry and introduces the fetal probe along the line to try to place the fetal sensors on the fetus' cheek. Unfortunately, the physician will only have tactile feedback in regards to the positioning of the sensors and will have no visual indication of the position of the fetal sensors relative to the fetus. If the physician has misassessed the position of the fetus and has not placed the fetal probe adjacent the fetus' cheek, the physician will have a difficult time in correctly positioning the fetal probe.

Accordingly, what is needed are systems and methods that provide visual feedback to the physician as to the orientation and position of the fetal probe sensors within the womb.

SUMMARY OF THE INVENTION

The present invention provides devices, systems and methods for providing visual feedback to aid in the proper placement of a fetal sensor during a fetal oximetry monitoring procedure. An imaging device, such as an optical fiber or fiber bundle, optical conduits, CCD camera, or the like can be coupled to a distal portion of the fetal probe to visually image and/or illuminate the same or nearby region of tissue which the fetal sensor contacts. The images from the illuminated portion of tissue are transmitted through the imaging device to an optical viewing device such as a hand-held image viewing instrument, camera, or a video monitor.

In exemplary embodiments, the fetal probe will include fetal oximetry sensors that have a light emitter (e.g., an LED) and a light detecting sensor. The light emitter can emit an infrared light, a visible light, or the like. In exemplary configurations, the imaging device can be positioned adjacent the fetal oximetry sensors so as to provide a visual indication of the position of the fetal sensors relative to the fetus' tissue.

In some arrangements, the LED can be used for emitting light for spectral pulse oximetry and for illuminating the fetus' tissue for visual examination. In other configurations, a separate illumination source (e.g., such as an optical fiber coupled to a broad spectrum light source) can be used to provide illumination for the visualization of the region of the fetus.

The light detecting sensors of the present invention will typically be configured to sense the light emitted from the light emitter for pulse oximetry purposes. In most arrangements the imaging device will be a separate component coupled to the distal portion of the probe. However, in some arrangements, the light detecting sensors can be configured to detect the light for visualization purposes. For example, a light sensor can vary its mode of operation to be able to both detect pulse oximetry data and to provide visual images of the fetus. In such embodiments, the pulse oximetry light detecting sensor will have a dual function and the separate imaging device will not be needed.

In a first aspect, the present invention provides a fetal probe. The fetal probe comprises a body. A fetal sensor is coupled to the body. An imaging assembly is positioned on the body to provide visual feedback of the position of the fetal sensor.

In one embodiment, focusing optics are coupled to the fetal sensor so as to provide a field of view and depth of field for the imaging device. In an exemplary embodiment, the imaging device includes a bundle of optical fibers. The optical fiber bundle may work in close proximity to the tissue being viewed so that no focusing element at the distal end is necessary. In most embodiments, the optical fiber bundle comprises a coherent arrangement of fibers (plastic or glass) to provide an image with the necessary resolution. Typically, the fiber bundle has a flexibility and diameter (approximately 1 mm to 3 mm) such that the fiber bundle can follow the turns and bends of the fetal sensor cable. Consequently, the flexible fiber bundle provides minimal discomfort to the patient during insertion. The proximal ends of the fiber bundle are typically attached to an eye piece, CCD camera with a video display, or other viewing devices. In most configurations, the viewing device can be adapted to alter the image orientation and/or provide magnification.

Appropriate attachments could be provided to permit easy removal of the optical fiber from the fetal sensor after completion of placement in utero. In alternative embodiments, the fiber bundle can be left attached to the fetal sensor and the viewing device can be disconnected from the proximal end of the fiber bundle. Such an arrangement would be particularly helpful if the optical fiber bundle is used to verify continued good placement of the fetal probe during the progress of labor.

In a particular embodiment, the present invention provides a fetal probe having a light emitter and a dual mode light detector. The light detector can function in at least two modes. In a first mode the light detector can detect light from the light emitter to provide a visualization of a fetus. In the second mode the light detector processes spectral oximetry data.

In another aspect, the present invention provides a method for positioning a fetal probe adjacent a fetus. The method comprises placing a fetal probe having a fetal sensor in close proximity to the fetus. A portion of at least one of the fetus and in utero environment is imaged with an imaging device that is coupled to the fetal probe. The image(s) are transmitted to a viewing device so as to provide a visual indication of the position of the fetal sensor.

In yet another aspect, the present invention provides a method for positioning a fetal probe adjacent a fetus. The method comprises advancing a fetal probe having a fetal sensor into contact with the fetus. The position of the fetal sensor is monitored with an imaging device that is attached to the fetal probe. The position of the fetal probe is adjusted if it is determined that the position of the fetal sensor is not adequate for monitoring the fetus.

For a further understanding of the nature and advantages of the invention, reference should be made to the following description taken in conjunction with the accompanying drawings.

BRIEF DESCRIPTION OF THE DRAWINGS

FIG. 1 is a plan view of a fetal probe of the present invention;

FIG. 2 is a partial cross sectional side view of the fetal probe of FIG. 1;

DESCRIPTION OF THE SPECIFIC EMBODIMENTS

Figure 3:
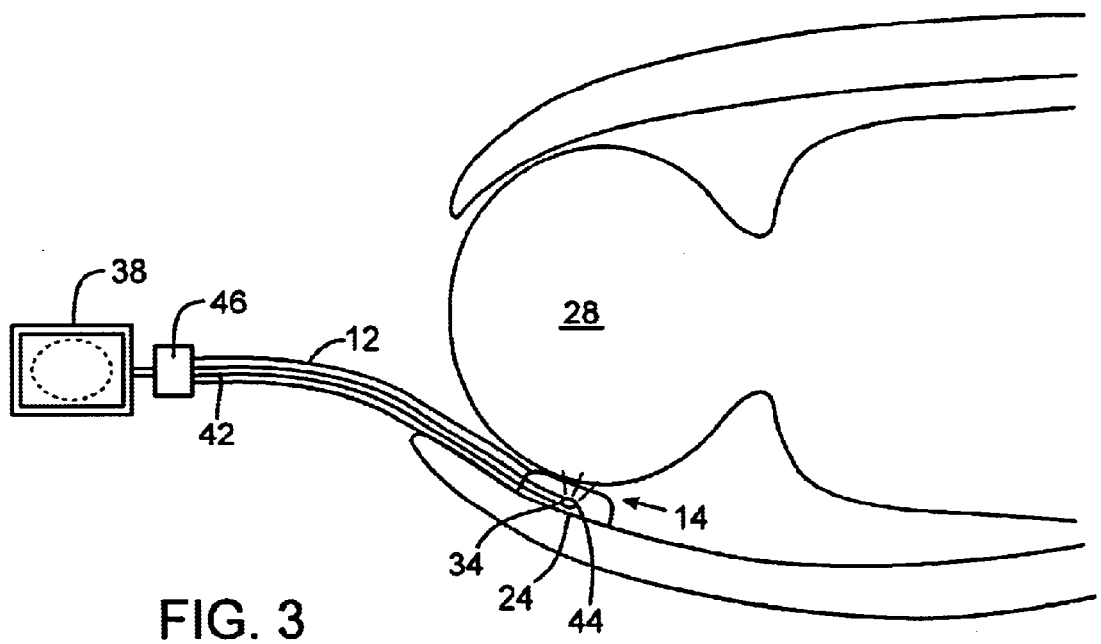
FIG. 3 illustrates placement of the fetal probe in the womb.

FIG. 1 illustrates a fetal probe 10 incorporating the present invention. The fetal probe 10 includes a shaft 12 which has a fetal sensor assembly 14 positioned at a distal body 16. In some embodiments, the shaft 12 may be detachable from the distal body 16. The distal body 16 is typically a sensor head that has a maternal surface 24 and a fetal surface 26 (FIG. 3). The fetal sensor 14 typically includes a light source 30 and a light detector 32. The light source 30 can be an LED that emits a light which can be in a variety of frequencies, including infrared and the visual spectrum. A light detector 32 is positioned on the fetal probe to receive the light from the light emitter to measure the blood characteristics of the fetus. An imaging device 34 is disposed on the distal end portion 16 of the shaft to provide visual feedback to the physician to aid in placement of the fetal sensor assembly 14. The light source 30 of the fetal sensor assembly 14 can be used to illuminate the region of the fetus imaged by the imaging device 34. A proximal end 36 of the imaging device 34 is coupled to a viewing device 38 to display images of a region of the fetus 28 and/or the surrounding in utero environment to the physician. A cable 18 connects the fetal sensor assembly 14 to a connector 20 that is disposed near a proximal end 22 of the shaft.

As shown in FIG. 2, the imaging device 34 can be positioned adjacent the light source 30 and the light detector 32 so as to image a region of tissue that is being optically probed by the oximetry system. It should be appreciated however, that the imaging device 34 can be positioned anywhere on the distal body 16. For example, as illustrated in FIG. 1, an imaging device 31 can be facing distally so as to monitor the position of the fetal probe in utero. Moreover, the concepts of the present invention are applicable to other fetal sensor assemblies. For example, the fetal sensor assembly can include a fetal oxygen saturation sensor, an ECG electrode, an intra-uterine pressure transducer, a temperature probe, or the like.

Imaging device 34 can be disposed within a recess 40 at the distal body 16 so as to provide space and a field of view, between the imaging device 34 and the fetus 28. In other embodiments, it may be desirable to position the imaging device 34 substantially along the surface of the distal body 16 so as to reduce the field of view.

In an exemplary embodiment, imaging device 34 is an optical fiber bundle having a proximal end 42 and a distal end 44 (FIG. 3). In most embodiments, the fiber bundle 34 comprises a coherent arrangement of fibers (plastic or glass) to produce an image with the necessary resolution and image quality to allow the physician to visualize the tissue adjacent the fetal sensor assembly 14. Typically, the fiber bundle has a flexibility and diameter (approximately 1 mm to 3 mm) such that the fiber bundle can follow the turns and bends of the fetal sensor cable 18. Consequently, the flexible fiber bundle provides minimal discomfort to the patient during insertion.

Focusing of the visual images of the fetus can be carried out in a variety of methods. For example, focusing optics can be employed at the distal end 44 of the imaging device 34 so as to provide an appropriate field of view and depth of field. Additionally or alternatively, focusing optics can be disposed at the proximal end of the imaging device. As another example, employing a gradient-index fiber of appropriate design, the fiber(s) themselves can act as a focusing element to focus and transmit an image of the fetus' tissue to the viewing device. Thus, there may be no need for focusing optics at the distal or proximal end of the imaging device. As an additional possibility, because the imaging device or fiber bundle may work in close proximity to the tissue being viewed, focusing optics may be unnecessary at the distal end. Thus, focusing optics can be employed at the proximal end to transmit the image to the viewing device. In yet another embodiment, a CCD can be coupled to a proximal end of an optical fiber of the imaging device to receive and focus the images of the fetus. From the above discussion, it should be appreciated that a variety of focusing methods and devices can be used to focus the images of the fetus.

Illumination of the fetus 28 can be provided through a separate illumination device (e.g., a single fiber or a bundle of optical fibers), through the light emitter 30 of the fetal sensor assembly, or through the same coherent imaging optical fiber bundle used for imaging the fetus. The illumination source can be standard broad spectrum light source, an infrared light source, or the like.

Appropriate attachments can be provided on the fetal probe to permit removal and attachment of the imaging device 34 from the fetal probe 10 after placement of the fetal probe adjacent the fetus 28. For example, once the fetal sensor assembly 14 has been placed adjacent the fetus 28 and it is determined that the sensor assembly is in good contact with the fetus, the imaging device 34 can be removed from the fetal probe 10. In alternative embodiments, the imaging device 34 can be integrated into the distal end portion of the fetal probe 24, 26 and the viewing device 38 (e.g., eye piece, video monitor, or the like) can be detached from a proximal end of the imaging device 34. Such an arrangement would be particularly helpful if the sensor assembly 14 is used to verify continued good placement of the fetal sensors during the progress of labor.

FIG. 3 illustrates the fetal probe 10 inserted into a mother's womb and positioned against the fetus 28. The shaft 12 can be a stiff cable that may have visual markings which indicate a depth of insertion. As can be seen, the fetal sensor assembly 14 could end up in a number of places where there is not a sufficient optical coupling with the fetus. For example, the fetal sensor assembly 14 can be positioned against the fetus' scalp or not in direct contact with the skin on the fetus' head 28 (i.e., amniotic fluid, blood, or vernix between the sensor and the fetus' head). The imaging device 34 positioned on the distal end of the fetal probe can provide visual feedback as to the placement of the fetal sensor assembly 14 and the quality of optical coupling.

Figure 4:
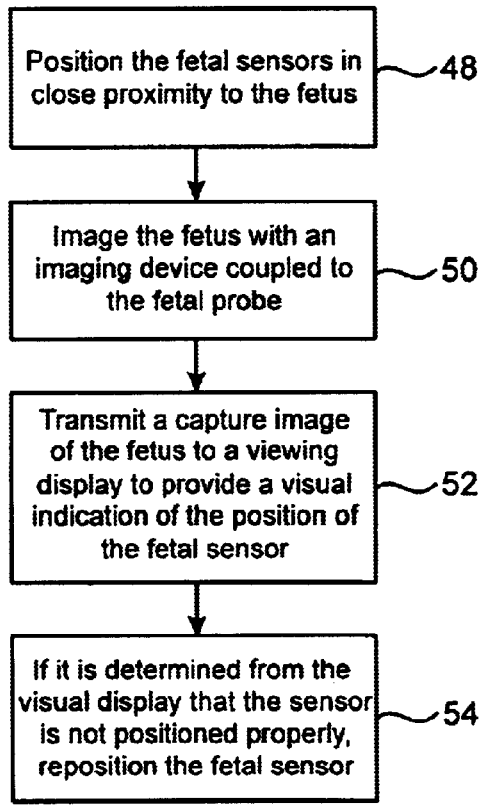
FIG. 4 is a flowchart of a method according to one embodiment of the present invention.

FIG. 4 illustrates a method of the present invention. The fetal probe is placed in close proximity to the fetus (step 48). The fetus is imaged with an imaging device that is coupled to the fetal probe (step 50). An image can be transmitted to a viewing device so as to provide a visual indication of the position of the fetal sensor (step 52).

If it is determined that the fetal sensor is not positioned against the fetus' head, or if it is determined that there is material (e.g., hair, mucous, vernix, or blood) that is between the fetal sensor and the fetus, the fetal sensor can be repositioned so that the fetal sensor can accurately detect the fetal blood characteristics, or other desired parameters (Step 54).

Optionally, it is possible to move the imaging device in utero to create a larger image of the fetus and the in utero environment. For example, a one-dimensional sensor or two dimensional sensor can be moved to effectively create a larger two dimensional "scan" of the fetus or in utero environment. The series of narrow images obtained by the sensor can thereafter be combined to create a larger field of view for the physician. If desired, the series of "narrow" images may be saved into a memory of a computer to create a scan of the fetus.

Figure 5:
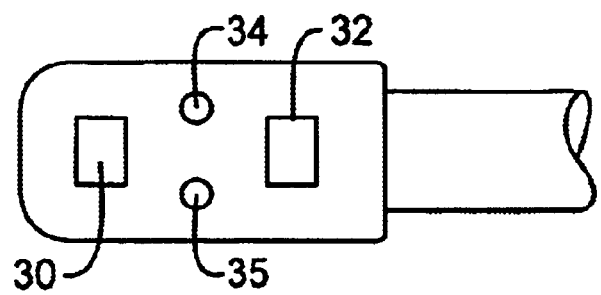
FIGS. 5–7 illustrate simplified distal ends of alternative embodiments of the fetal probe.
Figure 6:
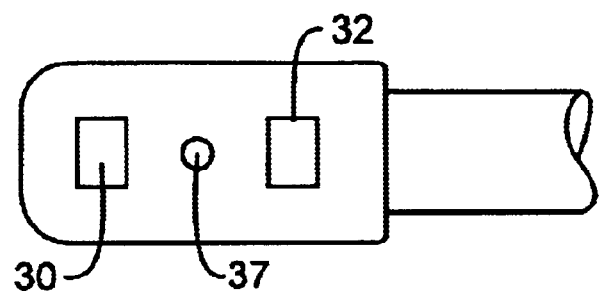
Figure 7:
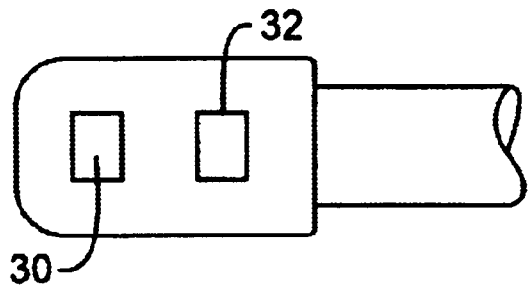

FIGS. 5–7 illustrate three specific embodiments of the present invention. FIG. 5 illustrates an embodiment in which the fetal probe 10 has a light emitter 30 that delivers a light for spectral oximetry and a light detector 32 for fetal oximetry measurements. An imaging device 34 and an additional light source 35 are disposed on the distal portion of the fetal probe to image and illuminate the region of the fetus.

FIG. 6 illustrates an embodiment of the fetal probe that has a light emitter 30 and a light detector 32 for fetal oximetry measurements. A separate light source 37, can deliver either infrared or broad spectrum light to the fetus to illuminate the region. The light detector 32 will be configured to deliver and process fetal oximetry data as well as to detect and deliver visual images to the physician.

FIG. 7 illustrates an embodiment of the fetal probe of the present invention in which both the light emitter 30 and light detector 32 are "dual mode" such that in one mode the light emitter can be used to illuminate the fetus while the light detector 32 delivers visual images of the fetus 28. Once it is determined that the fetal probe 10 is correctly positioned against the fetus, the mode of the light emitter 30 and light detector 34 can be changed to a second mode to measure the blood characteristics of the fetus.

As will be understood by those of skill in the art, the present invention may be embodied in other specific forms without departing from the essential characteristics thereof. For example, the imaging device can be a camera, or other optical device that can provide visual feedback to the placement of the fetal probe. Optionally, the fetal probes of the present invention can also include other conventional or proprietary mechanisms used in the art to improve the monitoring of the fetus. One such example is the use of a biasing mechanism, such as a fulcrum or balloon. Accordingly, the foregoing description is intended to be illustrative, but not limiting, of the scope of the invention which is set forth in the following claims.

What is claimed is:

1. A method of monitoring a fetus in an in utero environment, the method comprising:

providing a fetal probe comprising a proximal portion and a distal portion, the distal portion defining a first side and a second side that are positioned on opposed sides of a longitudinal axis of the distal portion, wherein a fetal sensor and an imaging assembly are positioned on the distal portion to monitor along the first side;

placing the fetal probe between the fetus and the in utero environment so that the first side is adjacent the fetus;

obtaining an image of the fetus to determine the positioning of the fetal sensor relative to the fetus; and transmitting an image to a viewing device to provide a visual indication of the position of the fetal sensor.

2. The method of 1 claim further comprising adjusting a position of the fetal probe upon determination that the fetal sensor is not in a proper position relative to the fetus.

3. The method of claim 1 comprising monitoring the fetus with the fetal sensor upon determining that the fetal sensor is properly positioned relative to the fetus.

4. The method of claim 1 further comprising:

contacting the fetal sensor with the portion of the fetus that is adjacent the fetal sensor; and illuminating the portion of the fetus that is in contact with the fetal sensor.

5. The method of claim 1 wherein the imaging assembly is an optical fiber bundle, wherein illuminating the fetus is through at least one optical fiber of the optical fiber bundle.

6. The method of claim 1 monitoring the position of the fetal probe during labor.

7. The method of claim 1 further comprising removing the imaging device from the fetal probe.

8. The method of claim 1 wherein imaging comprises moving the imaging device away from the fetus to create a larger field of view.

9. The method of claim 1 further comprising monitoring a depth of insertion of the fetal probe into the in utero environment.

10. The method of claim 1 wherein the proximal portion is flexible so as to allow insertion of the distal portion into the in utero environment.

11. A method of monitoring a fetus in an in utero environment, the method comprising:

providing a fetal probe comprising a proximal portion and a distal portion, the distal portion defining a first side and a second side that are positioned on opposed sides of a longitudinal axis of the distal portion, wherein a fetal oximetry sensor and an imaging assembly are positioned on the distal portion to monitor along the first side;

advancing the fetal probe into the in utero environment so that the first side faces the fetus;

imaging the fetus with the imaging assembly to monitor a position of the fetal oximetry sensor; and adjusting the position of the fetal probe if it is determined that the position of the fetal oximetry sensor is not adequate for desired monitoring of the fetus.

12. The method of claim 11 further comprising verifying placement of the fetal probe during labor.

13. The method of claim 11 further comprising scanning the fetus to create a larger field of view.

14. The method of claim 11 further comprising monitoring a depth of insertion of the fetal probe into the in utero environment.

15. The method of claim 11 wherein the proximal portion is flexible so as to allow insertion of the distal portion into the in utero environment.

* * * * *